| United States Patent [19] | [11] 4,339,598 |
|---|---|
| Guttmann et al. | [45] Jul. 13, 1982 |

[54] PREPARATION OF UNSATURATED ACIDS AND ESTERS FROM SATURATED CARBOXYLIC ACID DERIVATIVES AND CARBONYL COMPOUNDS OVER CATALYSTS CONTAINING V AND SB

[75] Inventors: Andrew T. Guttmann, Maple Heights; Robert K. Grasselli, Chagrin Falls, both of Ohio

[73] Assignee: SOHIO, Cleveland, Ohio

[21] Appl. No.: 221,588

[22] Filed: Dec. 31, 1980

[51] Int. Cl.³ .................. C07C 67/343; C07C 51/353
[52] U.S. Cl. ................................ 560/210; 562/599; 252/432; 252/456; 252/462; 252/464
[58] Field of Search .................. 560/211, 210, 214; 568/473, 474; 562/599

[56] References Cited

U.S. PATENT DOCUMENTS

| 1,895,529 | 1/1933 | Taylor et al. ................. 568/403 |
| 2,734,074 | 2/1956 | Redmon ....................... 560/210 |
| 3,014,958 | 12/1961 | Koch et al. ................... 560/210 |
| 3,051,747 | 8/1962 | Leathers et al. ............... 562/599 |
| 3,532,740 | 10/1970 | Hargis et al. .................. 560/214 |
| 4,165,438 | 8/1979 | Schneider ..................... 560/211 |

OTHER PUBLICATIONS

Birchall, T. et al., *Inorganic Chemistry*, vol. 15, (1976), pp. 868–870.

*Primary Examiner*—Natalie Trousof
*Assistant Examiner*—L. Hendriksen
*Attorney, Agent, or Firm*—David J. Untener; Herbert D. Knudsen; Larry W. Evans

[57] ABSTRACT

Vanadium-antimony catalysts have been found to be effective for the vapor phase condensation of saturated monocarboxylic acids or esters with formaldehyde, to produce unsaturated carboxylic acids or esters.

23 Claims, No Drawings

PREPARATION OF UNSATURATED ACIDS AND ESTERS FROM SATURATED CARBOXYLIC ACID DERIVATIVES AND CARBONYL COMPOUNDS OVER CATALYSTS CONTAINING V AND SB

BACKGROUND OF THE INVENTION

The condensation reaction of saturated carboxylic acids and esters with carbonyl compounds to produce unsaturated acids and esters is known in the art. U.S. Pat. No. 2,734,074 discloses that formaldehyde reacts with lower alkyl esters of aliphatic monocarboxylic acid to produce lower alkyl esters of alpha-beta unsaturated acids in the presence of a dehydration catalyst. Suitable catalysts found in this reference are lead chromate on silica gel, zinc chromite on silica gel, vanadia on alumina, zirconia on silica gel, or lead sulfate on silica gel.

U.S. Pat. No. 3,014,958 discloses an improvement upon this reaction by having present, in the reaction mixture, a substantial concentration of the desired unsaturated ester, generally exceeding about 7% of the weight of reactant ester. The reaction is again performed in the presence of a dehydration catalyst, suitable catalysts being phosphates of alkali and alkaline earths, aluminum and boron. Additionally, oxides, including mixed oxides of 20 additional metals are disclosed such as zinc, vanadium, chromium, molybdenum, tungsten, etc.

U.S. Pat. No. 4,165,438 discloses that acrylic acids and esters are produced by reacting a lower alkanoic acid or lower alkyl ester with formaldehyde in the presence of a vanadium orthophosphate catalyst having a specific surface area. For comparison purposes, this reference discloses inferior phosphate catalysts of lithium, sodium, magnesium, zinc, aluminum, chromium, cerium, niobium, antimony and bismuth.

Other catalysts useful in this reaction have been supported rare earth metal oxides disclosed in U.S. Pat. No. 3,701,798; X or Y zeolites with cesium, rubidium or potassium cations as found in U.S. Pat. No. 4,115,424; pyrogenic silica promoted with Groups IIA and IIIA metals disclosed in U.S. Pat. No. 3,933,888; and phosphates of magnesium, calcium, aluminum, zirconium, thorium or titanium as found in German Pat. No. 2,615,887.

SUMMARY OF THE INVENTION

The invention may be stated as a process for producing unsaturated carboxylic acids and esters which comprises passing into a reaction zone, a mixture of a saturated monocarboxylic acid or its ester with formaldehyde or a formaldehyde derivative, in the presence of a catalyst having the empirical formula $$VSb_mO_x$$

wherein
m = 0.5–40; and
x is determined by the nature and oxidation state of the other elements.

More specifically, the catalyst of the present invention may be promoted by various elements, thus having the empirical formula $$VSb_mA_aB_bC_cO_x$$

where
m = 0.5–40, preferably 3–15, and
A = alkali metal, alkaline earth metal, Tl, La, rare earth metal, Th, or mixtures thereof,
B = Cu, Ag, Fe, Co, Ni, Mn, Cr, Nb Ta, Ti, As, Sn, B, U or mixtures thereof,
C = Mo, W, Te, Bi, or mixtures thereof; and
a = 0–1;
b = 0–1;
c = 0–1; and
x = is determined by the nature and oxidation state of the other elements.

Preferably, the sum (a+b+c) is smaller than m and also equal to or smaller than 2.

As noted in the Background, the condensation reaction itself is known in the art and may be expressed by the following equation using methyl acetate as an example:

$$H_2CO + H_3C-COOCH_3 \rightarrow H_2C=CH-COOCH_3 + H_2O$$

It is conveniently carried out by mixing formaldehyde in a suitable form with the appropriate acid or ester, e.g. methyl acetate in the desired ratio, vaporizing the mixture, and passing the vapors continuously over the catalyst. Fixed or fluid bed operation is possible. Steam or inert diluents may be added (e.g. $N_2$). Commercial aqueous or alcoholic $CH_2O$ solutions, formals such as methylal, or volatile $(CH_2O)_x$ compounds, such as s-trioxane, may serve as a formaldehyde source. Alternately, the gaseous product effluent from a formaldehyde manufacturing process unit (e.g. by methanol oxidation) may be passed over a catalyst of this invention, along with the vapors of the appropriate ester or acid.

Preferably, formaldehyde, including formaldehyde derivatives, polymers, oligomers, and precursors thereof are condensed with acetic acid or acetates, or with propionic acid or propionates. A preferred aspect of the invention is to prepare acrylic acid and methacrylic acid derivatives from formaldehyde and acetic-/propionic acid and their esters.

The reaction temperature may range from 200° to about 450° C., preferably from 300°–350° C. The average residence time may be from about 2 to about 30 seconds, preferably from 3 to 15 seconds. The molar ratio of acid or esters to formaldehyde may range from 0.1 to about 10.

The catalysts may be used unsupported, but the use of a suitable carrier, such as silica, alumina, mixtures of silica and alumina, amorphous silica-alumina, crystalline aluminosilicates, titania, natural clays and such is preferred. Especially good results are obtained with silica and alumina mixtures as support. The concentration of the active catalyst on the support may range from about 10 to about 80% by weight.

The catalysts are conveniently prepared by procedures similar to the synthesis of vanadium orthoantimonate (Birchall and Sleight, *Inorganic Chemistry*, Vol. 15, pages 868-70, 1976) involving a redox reaction such as $$V_2P_5 + Sb_2O_3 \rightarrow 2VSbO_4$$

in which pentavalent vanadium is reduced, while the trivalent antimony of $Sb_2O_3$ is oxidized to the pentavalent state. The $V_2O_5$ can be replaced by ammonium metavanadate, or other compounds of pentavalent vanadium.

It may be advantageous for catalytic performance to employ an excess of antimony trioxide over the stoichiometric amount in the preparation of the catalysts of the invention. Such excess of $Sb_2O_3$ will, during the calcination of the catalyst at a high temperature in air, be oxidized to $Sb_2O_4$ and/or $Sb_2O_5$, $Sb_6O_{13}$ and the like. Thus, the catalytic composition contains all or part of the vanadium in an oxidation state of less than $+5$ and most of the antimony in the oxidation states of $+4$ and $+5$.

The catalysts of the invention may be prepared by heating an intricate mixture of the dry reactants. However, it is preferred to prepare an aqueous solution or slurry of, for example, ammonium metavanadate and $Sb_2O_3$, boil it under reflux for 6–16 hours, followed by addition of a support, $Al_2O_3$ or $SiO_2$, and any additional promoting elements in the form of their salts, oxides, hydroxides, acids, or other components. The slurry is then evaporated, dried, subjected to additional heat treatment as needed, and calcined at from 350° to 850° C., preferably from 450° to 750° C. In a modification, the excess antimony over the stoichiometric amount may be added as $Sb_2O_5$ instead of $Sb_2O_3$. In such a case the $Sb_2O_5$ is preferably added to the slurry after the initial reaction of $Sb_2O_3$ with the stoichiometric amount of e.g. ammonium metavanadate (including the reflux period). Good results are obtained when an aqueous colloidal $Sb_2O_5$ sol is used.

Alternately, the catalysts may be prepared by reducing the pentavalent vanadium compound separately by treatment with an alcohol, such as benzyl alcohol or isobutanol, with or without addition of HCl, followed by reaction with a compound of pentavalent antimony. Addition of supports and any promoting elements will proceed in a manner analogous to the previous procedure.

REACTION OF METHYL ACETATE WITH METHYLAL

EXAMPLES 1–10

The catalyst of Example 1, having the composition $42\% K_{0.4}VSb_5O_x, -42\% Al_2O_3$, and $16\% SiO_2$ was prepared as follows. A slurry of 41.9 g $Sb_2O_3$ in 190 ml $H_2O$ was heated to 75° C., and a hot solution of 6.7 g $NH_4VO_3$ was added with stirring. The mixture was boiled with reflux overnight. A solution of 1.59 $K_2CO_3$ in 10 ml water was then added, followed by 58.6 g hydrated alumina (Catapal SB, 85% $Al_2O_3$), and 47.5 g 40% silica sol. The mixture was stirred in an open beaker, evaporated at 85°–90° C., and dried at 120°–125° C., ground and screened to 20/35 mesh size, and calcined 5 hours at 550° C.

In the same manner, catalysts of Examples 2–8 were prepared having the composition shown in Table I. Examples 9–10 show catalysts where the excess antimony was added as $Sb_2O_5$ after the reflux step.

Five cc of the catalyst was charged to a fixed-bed micro-reactor equipped with a preheat leg serving as a vaporizer, and immersed in a temperature controlled salt bath at 330° C. Liquid feed consisting of a mixture of methylacetate and methylal (formaldehyde dimethyl acetal) in a molar ratio of 10:1 was injected by a syringe pump into the reactor, through the preheat leg, over a period of 70 minutes, at such a rate that the feed vapors passed over the catalyst at an average contact time of 10 seconds. The reactor effluent was condensed, weighed, and analyzed by gas chromatography. The results are shown in Table I as per pass conversion based on methylal.

REACTION OF METHYL PROPIONATE WITH METHYLAL

EXAMPLES 11–16

In the same manner of Example 1, catalysts of Examples 11–14 and 16 were prepared on varying supports as shown in Table II. For example 15, excess antimony was added as $Sb_2O_5$. All catalysts were calcined at a temperature of 550° C., except Example 12 calcined at 350° C. and Example 13 at 650° C.

In the reactor of Example 1, a feed of methyl propionate/methylal at a ratio of 10/1 was passed over the catalyst. The reaction temperature was 330° C. with a contact time of 10 seconds. For Examples 11 and 12, the reactor was on stream 90 minutes; Example 14 for 30 minutes; and Examples 13, 15 and 16 for 60 minutes. The results are shown in Table II.

REACTION OF ACETIC ACID WITH FORMALDEHYDE

EXAMPLE 17

In the same manner of the previous Examples, the catalyst of Example 4 was utilized in the reaction of acetic acid with formaldehyde. Acetic acid/aqueous formaldehyde/nitrogen in a ratio of 10/1/5 was passed over the catalyst at a temperature of 330° C. and a contact time of ten seconds. Per pass conversion to acrylic acid was 25.1%.

REACTION OF PROPIONIC ACID WITH TRIOXANE

EXAMPLE 18

The catalyst of Example 16 was utilized in the reaction of propionic acid with trioxane. Propionic acid/trioxane/steam in a ratio of 10/1/1 was passed over the catalyst at a temperature of 330° C. and a contact time of 10 seconds. Per pass conversion to methacrylic acid was 34.4%.

TABLE I

| | Reaction of Methyl Acetate with Methylal Over V-Sb Catalysts | | | |
|---|---|---|---|---|
| | | % Conver. | % PPC | | |
| Example | Catalyst | Methylal | Methyl Acrylate | Acrylic Acid | Total |
| 1 | $K_{0.4}VSb_5O_x$ | 100 | 51.0 | 2.7 | 53.7 |
| 2 | $K_{0.4}VSb_{15}O_x$ | 99.9 | 49.5 | 4.1 | 53.6 |
| 3 | $K_{0.4}Cu_{0.5}VSb_5O_x$ | 99.1 | 31.2 | 3.7 | 34.9 |
| 4 | $K_{0.4}Ag_{0.5}VSb_5O_x$ | 100 | 42.2 | 3.2 | 45.4 |
| 5 | $K_{0.4}Fe_{0.5}VSb_5O_x$ | 100 | 37.2 | 2.6 | 39.8 |
| 6 | $K_{0.4}Mo_{0.5}VSb_5O_x$ | 99.1 | 32.0 | 2.2 | 34.2 |
| 7 | $U_{0.5}VSb_5O_x$ | 100 | 46.2 | 6.7 | 42.9 |
| 8 | $VSb_{13}O_x$ | 99.8 | 50.9 | 3.7 | 54.6 |

TABLE I-continued

Reaction of Methyl Acetate with Methylal Over V-Sb Catalysts

| Example | Catalyst | % Conver. Methylal | % PPC Methyl Acrylate | Acrylic Acid | Total |
|---------|----------|--------------------|------------------------|--------------|-------|
| 9 | $VSb_{10}O_x$ | 100 | 41.3 | 6.5 | 47.8 |
| 10 | $VSb_5O_x$ | 100 | 45.7 | 5.7 | 51.4 |

TABLE II

REACTION OF METHYL PROPIONATE WITH METHYLAL OVER V-Sb CATALYSTS

| Example | Catalyst | Support | % Conv. Methylal | Methyl Methacrylate | Acid | Total |
|---------|----------|---------|------------------|---------------------|------|-------|
| 11 | 50% $VSb_5O_x$ | $SiO_2$ | 9.1 | 4.8 | 0 | 4.8 |
| 12 | 50% $VSb_5O_x$ | $TiO_2$ | 7.0 | 2.3 | 0 | 2.3 |
| 13 | 50% $VSb_5O_x$ | $Al_2O_3$ | 90.3 | 18.3 | 1.8 | 20.1 |
| 14 | 50% $VSb_5O_x$ | $Al_2O_3$ | 85.5 | 45.1 | 2.5 | 47.6 |
| 15 | 42% $VSb_5O_x$ | 42% $Al_2O_3$/16% $SiO_2$ | 96.7 | 43.1 | 2.2 | 45.3 |
| 16 | 42% $K_{0.4}VSb_5O_x$ | 42% $Al_2O_3$/16% $SiO_2$ | 91.6 | 47.5 | 3.6 | 51.1 |

We claim:

1. A process for producing unsaturated carboxylic acid and esters which comprises passing into a reaction zone, a vaporous mixture of a saturated monocarboxylic acid or its ester with a compound selected from the group consisting of formaldehyde, Formaldehyde acetals, or volatile formaldehyde polymers, at a temperature of from 200° C. to about 450° C., in the presence of a catalyst having the empirical formula $$VSb_mO_x$$

wherein m=0.5–40; and x is determined by the nature and oxidation state of the other elements.

2. The process of claim 1 wherein m is 3–15.

3. The process of claim 1 wherein the catalyst is on a support comprising alumina and silica.

4. A process for producing unsaturated carboxylic acids and esters which comprises passing into a reaction zone, a vaporous mixture of a saturated monocarboxylic acid or its ester with a compound selected from the group consisting of formaldehyde, Formaldehyde acetals, or volatile formaldehyde polymers, at a temperature of from 200° C. to about 450° C., in the presence of a catalyst having the empirical formula $$VSb_mA_aB_bC_cO_x$$

wherein m=0.5–40; and

A=alkali metal, alkaline earth metal, Tl, La, rare earth metal, Th, or mixtures thereof, B=Cu, Ag, Fe, Co, Ni, Mn, Cr, Nb, Ta, Ti, As, Sn, B, U or mixtures thereof, C=Mo, W, Te, Bi, or mixtures thereof;

and a=0–1;
b=0–1;
c=0–1, x is determined by the nature and oxidation state of the other elements.

5. The process of claim 4 wherein m is 3–15.

6. The process of claims 2 and 5 wherein the formaldehyde derivative is methylal.

7. The process of claims 2 and 5 wherein the formaldehyde derivative is trioxane.

8. The process of claims 2 and 5 wherein the saturated monocarboxylic acid is acetic acid.

9. The processes of claims 2 and 5 wherein the saturated monocarboxylic acid is propionic acid.

10. The process of claims 2 and 5 wherein the ester fed to the reaction zone is methylacetate.

11. The process of claims 2 and 5 wherein the ester fed to the reaction zone is methylpropionate.

12. The process of claim 5 wherein A is an alkali metal.

13. The process of claim 12 wherein A is potassium.

14. The process of claim 5 wherein B is Cu.

15. The process of claim 5 wherein B is Ag.

16. The process of claim 5 wherein B is Fe.

17. The process of claim 5 wherein C is Mo.

18. The process of claim 5 wherein B is U.

19. The process of claims 14, 15, 16, 17 and 18 wherein A is an alkali metal.

20. The process of claim 4 wherein the catalyst is on a support comprising alumina and silica.

21. The process of claim 1 wherein the catalyst is on a support comprising alumina.

22. The process of claim 4 wherein the catalyst is on a support comprising alumina.

23. The process of claim 4 wherein the sum (a+b+c) is smaller than m and equal to or smaller than 2.

* * * * *